(12) United States Patent
Kevil et al.

(10) Patent No.: US 12,280,058 B2
(45) Date of Patent: Apr. 22, 2025

(54) GASOTRANSMITTER METABOLITES AND ALZHEIMER'S DISEASE

(71) Applicant: Board of Supervisors of Louisiana State University and Agricultural and Mechanical College, Baton Rouge, LA (US)

(72) Inventors: Christopher Kevil, Shreveport, LA (US); Elizabeth Disbrow, Shreveport, LA (US); Jonathan Steven Alexander, Shreveport, LA (US); Karen Y. Stokes, Shreveport, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 697 days.

(21) Appl. No.: 17/200,746

(22) Filed: Mar. 12, 2021

(65) Prior Publication Data

US 2021/0285938 A1  Sep. 16, 2021

Related U.S. Application Data

(60) Provisional application No. 62/988,522, filed on Mar. 12, 2020.

(51) Int. Cl.
*A61K 31/195* (2006.01)
*A61K 31/198* (2006.01)
(Continued)

(52) U.S. Cl.
CPC ............ *A61K 31/53* (2013.01); *A61K 31/195* (2013.01); *A61K 31/198* (2013.01); *G01N 33/84* (2013.01); *G01N 2800/2821* (2013.01)

(58) Field of Classification Search
CPC ..... A61K 31/53; A61K 31/195; A61K 31/198; G01N 33/84; G01N 2800/2821
See application file for complete search history.

(56) References Cited

U.S. PATENT DOCUMENTS

| 5,112,598 A | 5/1992 | Biesalski |
| 5,556,611 A | 9/1996 | Biesalski |

(Continued)

FOREIGN PATENT DOCUMENTS

| WO | WO-2014201446 A2 * | 12/2014 | ........... A61K 31/195 |
| WO | WO-2020172288 A1 * | 8/2020 | ........... A23L 33/135 |

OTHER PUBLICATIONS

Wang, I157172, a novel inhibitor of cystathionine y-lyase, inhibits growth and migration of breast cancer cells via SIRT1-mediated deacetylation of STAT3, Jan. 2019, Oncology Reports 41: 427-436 (Year: 2019).*

(Continued)

*Primary Examiner* — Samuel P Siefke
*Assistant Examiner* — Valerie Simmons
(74) *Attorney, Agent, or Firm* — Baker, Donelson, Bearman, Caldwell, & Berkowitz, PC

(57) ABSTRACT

A method of diagnosing Alzheimer's disease and related dementias (ADRD) in a patient comprising obtaining a plasma sample from the patient; determining a level of a biochemical sulfide in the plasma sample from the subject by trapping volatilized $H_2S$ in the plasma sample using alkaline buffer with monobromobiamine, and detecting the level of biochemical sulfide in the plasma sample, the biochemical sulfide being one of acid-labile sulfide, bound sulfide, and total sulfide; and diagnosing the patient with ADRD when the level of the biochemical sulfide is at least an elevated threshold level for the biochemical sulfide.

3 Claims, 9 Drawing Sheets

(51) Int. Cl.
A61K 31/53 (2006.01)
G01N 33/84 (2006.01)

(56) References Cited

U.S. PATENT DOCUMENTS

2009/0233888 A1* 9/2009 Lin .................. A61K 35/413 436/119
2018/0271802 A1* 9/2018 Kevil .................. A61K 31/105
2018/0275115 A1* 9/2018 Kevil .................. G01N 30/8675

OTHER PUBLICATIONS

Fuqin, Pharmacological targeting of kinases MST1 and MST2 augments tissue repair and regeneration, 2016, www.ScienceTranslationalMedicine.org Aug. 17, 2016 vol. 8 Issue 352 352ra108 (Year: 2016).*
Abe, The Possible Role of Hydrogen Sulfide as an Endogenous Neuromodulator, 1996, The Journal of Neuroscience, Feb. 1, 1996, 76(3):1066-i 071 (Year: 1996).*
Berge, S. M. et al. Pharmaceutical Salts. J Pharmaceutical Sciences, 66:1-19 (1977).
Giovinazzo, D. et al. Hydrogen sulfide is neuroprotective in Alzheimer's disease by sulfhydrating GSK3β and inhibiting Tau hyperphosphorylation. PNAS, 118(4), e2017225118, 8 pages (2011).
Giovinazzo, J. et al. 4D-imaging of drip-line radioactivity by detecting proton emission from 54mNi pictured with ACTAR TPC. Nature Communications, vol. 12, Article No. 4805, (2021).
Guide for Care and Use of Laboratory Animals, 8th ed., the National Academies Press, Washington, DC, 246 pages (2011).
Higuchi, T. and Stella, V. (eds.) Pro-drugs as Novel Delivery Systems. A.C.S. Symposium Series, vol. 14, Am. Chemical Society, Washington DC (1975).
RPART algorithm. Webpage https://cran.r-project.org/web/packages/rpart/rpart.pdf, published Dec. 5, 2003, 34 pages.
Shen, X. et al. Measurement of H2S In Vivo and In Vitro by the Monobromobimane Method. Methods in Enzymology, 554C, 31-45 (2015).
Stahl, P. H. et al. (eds). Pharmaceutical Salts: Properties, Selection, and Use. Wiley-VCR, Zurich (2008).
Swarbrick, J. and Boyland, J. C. (eds.) Encyclopedia of Pharmaceutical Technology, vol. 20, part 1, 240 pages (2001).
Swarbrick, J. and Boyland, J. C. (eds.) Encyclopedia of Pharmaceutical Technology, vol. 20, part 2, 95 pages (2001).
Yang, C.T. et al. Data-Driven Identification of Hydrogen Sulfide Scavengers. Angewandte Chem. Int. Ed. Engl., 58 (32):10898-10902 (2019).
Gennaro et al. (eds) Remington: The Science and Practice of Pharmacy, 20nd Ed., Lippencott Williams & Wilkins (2000).
Harris, D. et al. Drug delivery via the mucous membranes of the oral cavity. Journal of Pharmaceutical Sciences, 81(1):1-10 (1992).

* cited by examiner

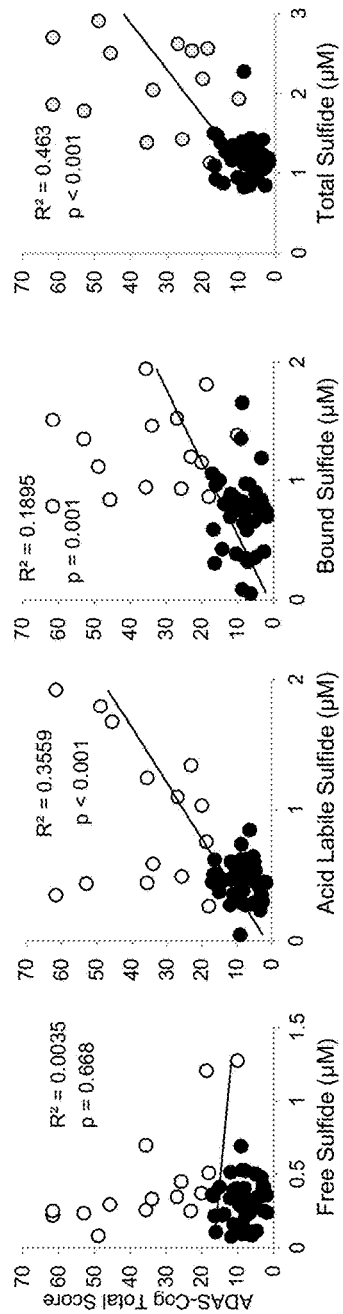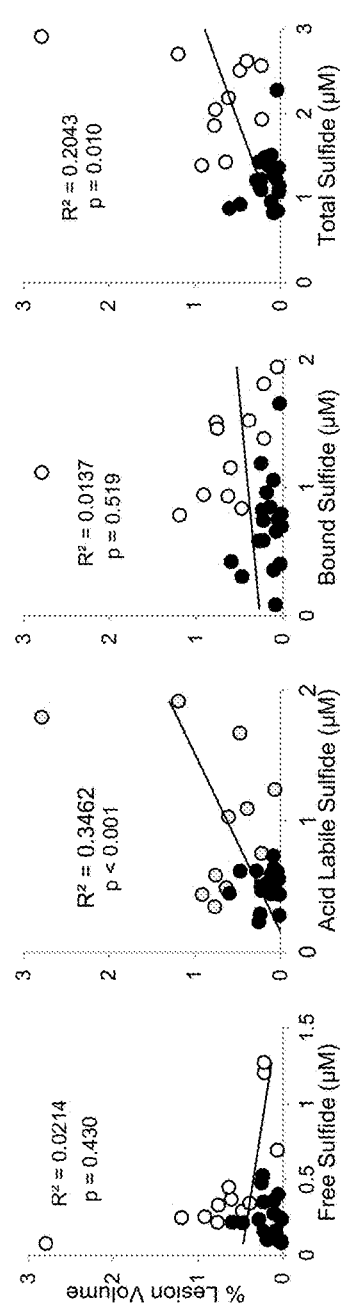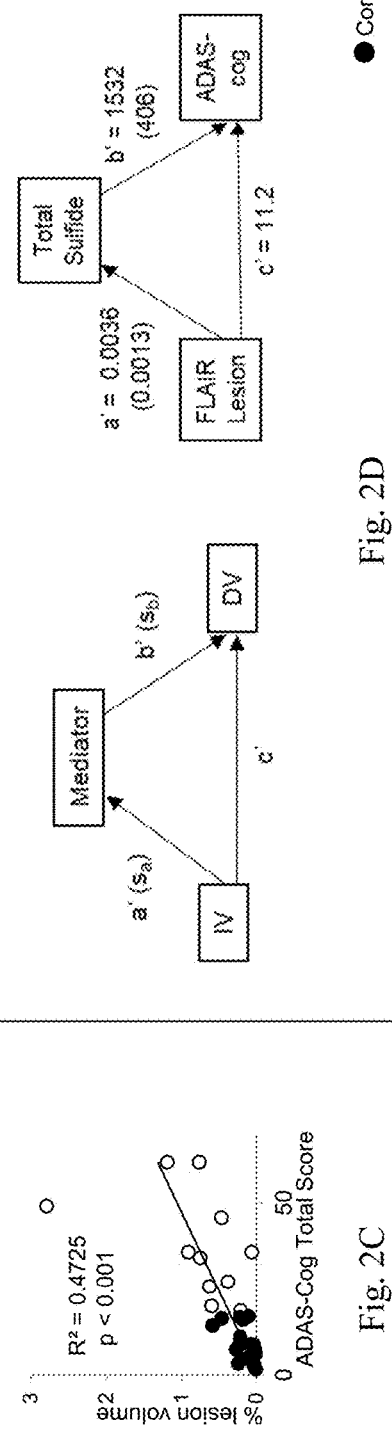
Fig. 2A
Fig. 2B
Fig. 2C
Fig. 2D

| Variable | All | Total H₂S Metabolites | All (N=MRI-only) | Total H₂S (N=MRI-only) |
|---|---|---|---|---|
| Accuracy | 0.929825 | 0.929825 | 0.903226 | 0.903226 |
| Sensitivity | 0.8 | 0.8 | 0.833333 | 0.833333 |
| False Neg. Rate | 0.2 | 0.2 | 0.166667 | 0.166667 |
| Specificity | 0.97619 | 0.97619 | 0.947368 | 0.947368 |
| False Pos. Rate | 0.02381 | 0.02381 | 0.052632 | 0.052632 |
| Pos. Pred. Value | 0.923077 | 0.923077 | 0.909091 | 0.909091 |
| False Disc. Rate | 0.076923 | 0.076923 | 0.090909 | 0.090909 |
| False Omit. Rate | 0.068182 | 0.068182 | 0.1 | 0.1 |
| Neg. Pred. Value | 0.931818 | 0.931818 | 0.9 | 0.9 |
| Candidate Dimensions | 10 | 5 | 10 | 5 |

| | N | Age (years) | Education (years) | ADAS Score* |
|---|---|---|---|---|
| ADRD Total | 15 (13 female, 7 AA) | 68.47 (5.93) | 14.80 (2.68) | 34.65 (16.31) |
| Control Total | 42 (36 female, 19 AA) | 67.50 (9.65) | 15.90 (2.16) | 8.40 (4.25) |
| ADRD MRI | 12 (10 female, 7AA) | 67.42 (4.10) | 14.00 (2.24) | 35.38 (16.50) |
| Control MRI | 19 (16 female, 12 AA) | 63.47 (7.54) | 16.15 (2.21) | 8.85 (5.00) |

Fig. 7

| Edu. | ADAS | Brain Vol. | Hippo. % Vol. | Ventricle % Vol. | Gray % Vol. | White % Vol. | Lesion % Vol. | Plasma Free H$_2$S | Acid Labile H$_2$S | Plasma Bound H$_2$S | Plasma Total H$_2$S | | |
|---|---|---|---|---|---|---|---|---|---|---|---|---|---|
| 0.172 | 0.036 | -0.339 | -0.053 | 0.252 | 0.078 | -0.055 | 0.170 | 0.205 | -0.189 | 0.065 | -0.077 | Corr. | Age |
| 0.200 | 0.792 | 0.062 | 0.778 | 0.172 | 0.675 | 0.769 | 0.359 | 0.126 | 0.158 | 0.630 | 0.567 | Sig. | |
| 57 | 57 | 31 | 31 | 31 | 31 | 31 | 31 | 57 | 57 | 57 | 57 | N | |
| | -0.125 | .398* | 0.280 | -0.059 | 0.253 | -0.224 | -.394* | -0.098 | -.371** | -0.110 | -.314* | Corr. | Edu. |
| | 0.353 | 0.027 | 0.127 | 0.752 | 0.169 | 0.226 | 0.028 | 0.467 | 0.004 | 0.415 | 0.018 | Sig. | |
| | 57 | 31 | 31 | 31 | 31 | 31 | 31 | 57 | 57 | 57 | 57 | N | |
| | | -.378* | -.418* | .727** | -0.343 | 0.334 | .687** | -0.059 | .596** | .436** | .681** | Corr. | ADAS |
| | | 0.036 | 0.019 | 0.000 | 0.059 | 0.067 | 0.000 | 0.664 | 0.000 | 0.001 | 0.000 | Sig. | |
| | | 31 | 31 | 31 | 31 | 31 | 31 | 57 | 57 | 57 | 57 | N | |
| | | | 0.013 | -.378* | 0.051 | -0.008 | -0.274 | 0.011 | -0.253 | -0.299 | -.361* | Corr. | Brain Vol. |
| | | | 0.943 | 0.036 | 0.787 | 0.964 | 0.136 | 0.953 | 0.169 | 0.102 | 0.046 | Sig. | |
| | | | 31 | 31 | 31 | 31 | 31 | 31 | 31 | 31 | 31 | N | |
| | | | | -.368* | .406* | -.455* | -0.320 | 0.044 | -0.186 | -0.056 | -0.155 | Corr. | Hippo. % Vol. |
| | | | | 0.042 | 0.023 | 0.010 | 0.079 | 0.814 | 0.317 | 0.767 | 0.405 | Sig. | |
| | | | | 31 | 31 | 31 | 31 | 31 | 31 | 31 | 31 | N | |
| | | | | | 0.017 | -0.006 | .494** | -0.114 | 0.212 | 0.200 | 0.269 | Corr. | Ventricle % Vol. |
| | | | | | 0.928 | 0.973 | 0.005 | 0.543 | 0.252 | 0.281 | 0.144 | Sig. | |
| | | | | | 31 | 31 | 31 | 31 | 31 | 31 | 31 | N | |

Fig. 8A

| | White %Vol. | Lesion %Vol. | Plasma Free H2S | Acid Labile H2S | Plasma Bound H2S | Plasma Total H2S |
|---|---|---|---|---|---|---|
| Edu. — Corr. | -.990** | -.416* | 0.253 | -0.303 | -0.009 | -0.199 |
| Edu. — Sig. | 0.000 | 0.020 | 0.169 | 0.097 | 0.960 | 0.284 |
| Edu. — N | 31 | 31 | 31 | 31 | 31 | 31 |
| ADAS — Corr. | | .399* | -0.231 | 0.266 | 0.002 | 0.170 |
| ADAS — Sig. | | 0.026 | 0.212 | 0.149 | 0.992 | 0.361 |
| ADAS — N | | 31 | 31 | 31 | 31 | 31 |
| Lesion %Vol. — Corr. | | | -0.146 | .588** | 0.117 | .452* |
| Lesion %Vol. — Sig. | | | 0.433 | 0.000 | 0.530 | 0.011 |
| Lesion %Vol. — N | | | 31 | 31 | 31 | 31 |
| Plasma Free H2S — Corr. | | | | -0.129 | .429** | 0.210 |
| Plasma Free H2S — Sig. | | | | 0.338 | 0.001 | 0.118 |
| Plasma Free H2S — N | | | | 57 | 57 | 57 |
| Acid Labile H2S — Corr. | | | | | 0.139 | .738** |
| Acid Labile H2S — Sig. | | | | | 0.304 | 0.000 |
| Acid Labile H2S — N | | | | | 57 | 57 |
| Plasma Bound H2S — Corr. | | | | | | .771** |
| Plasma Bound H2S — Sig. | | | | | | 0.000 |
| Plasma Bound H2S — N | | | | | | 57 |

Fig. 8B

GASOTRANSMITTER METABOLITES AND ALZHEIMER'S DISEASE

CROSS REFERENCE TO RELATED APPLICATIONS/PRIORITY

The present invention claims priority to United States Provisional Patent Application No. 62/988,522 filed Mar. 12, 2020, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

STATEMENT REGARDING FEDERALLY SPONSORED RESEARCH OR DEVELOPMENT

This invention was made with government support under Grant No. P20 GM121307 awarded by the National Institutes of Health. The government has certain rights in the invention.

BACKGROUND

While heart disease remains the most common cause of worldwide mortality, Alzheimer's disease and related dementias (ADRD) are estimated to affect more than 5 million people in the U.S. and more than 47 million people worldwide. The toll on individuals, caregivers and society is enormous and will only increase as the population ages. ADRD are conditions that can begin many years before outward symptoms manifest. Early intervention, even if just forestalling the eventual disease, has significant economic and societal benefits. In spite of this, there is currently a lack of reliable and affordable early tests for ADRD. For the foregoing reasons, there is a pressing, but seemingly irresolvable need for a reliable early test for ADRD.

SUMMARY

Wherefore, it is an object of the present invention to overcome the above-mentioned shortcomings and drawbacks associated with the current technology.

The presently disclosed invention relates to machines, therapeutics and methods of diagnosing Alzheimer's disease and related dementias (ADRD) in a patient comprising obtaining a plasma sample from the patient, determining a level of a biochemical sulfide in the plasma sample from the patient by trapping volatilized $H_2S$ in the plasma sample using alkaline buffer with monobromobiamine, and detecting the level of the biochemical sulfide in the plasma sample, the biochemical sulfide being one of acid-labile sulfide, bound sulfide, and total sulfide, and diagnosing the patient with ADRD when the level of the biochemical sulfide is at least an elevated threshold level for the biochemical sulfide. According to a further embodiment the biochemical sulfide is total sulfide. According to a further embodiment the elevated threshold level is 1.32 µM. According to a further embodiment the elevated threshold level is 1.64 µM. According to a further embodiment the method further comprises determining a level of free sulfide in the plasma, and only diagnosing the patient with ADRD if both the level of free sulfide is a normal level and the level of the biochemical sulfide is at least an elevated threshold level for the biochemical sulfide. According to a further embodiment the normal level of free sulfide is less than 0.80 µM. According to a further embodiment the normal level of free sulfide is less than 0.70 µM. According to a further embodiment the biochemical sulfide is total sulfide and the elevated threshold level is 1.32 µM The presently disclosed invention further relates to machines, therapeutics and methods of diagnosing and treating Alzheimer's disease and related dementias (ADRD) comprising obtaining a plasma sample the patient, determining a level of a biochemical sulfide in the plasma sample from the patient, the biochemical sulfide being one of acid-labile sulfide, bound sulfide, and total sulfide, diagnosing the patient with ADRD when biochemical sulfide is above a cutoff, and administering an effective amount of a sulfide reducer to the diagnosed patient. According to a further embodiment the sulfide reducer is one of a sulfide scavenger, a CSE inhibitor, a CBS inhibitor, an MST inhibitor, and a NO promotor. According to a further embodiment the sulfide reducer is a CSE inhibitor and includes one of L-propylarginine, L-aminoethoxyvinylglycine, and β-cyanoalanine, 1157172 (2-[(4-(2,5-dimethoxyanilino)-6-(3-nitroanilino)-1,3,5-triazin-2-yl) sulfanyl]-6-ethoxy-1,3-benzothiazole. According to a further embodiment the sulfide reducer is a CBS inhibitor and includes one of hydroxylamine, aminooxyacetic acid, trifluoroalanine, L-aminoethoxyvinylglycine, and both L-aminoethoxyvinylglycine and pyridoxamine. According to a further embodiment the sulfide reducer is an MST inhibitor and includes XMU-MP-1 (4-((5,10-dimethyl-6-oxo-6,10-dihydro-5H-pyrimido[5,4-b]thieno[3,2-e][1,4]diazepin-2-yl)amino)benzenesulfonamide). According to a further embodiment the sulfide reducer is a NO promotor and includes one of DEA/NO, DETA/NO, and Sper/NO administered at concentrations up to 50 uM or sodium nitrite administered in an amount from 165 µg/kg to 1.65 mg/kg mass sodium nitrite to mass patient. According to a further embodiment the sulfide reducer is administered at a dose and a duration until the level of biochemical sulfide was brought to below 1.70 µM. According to a further embodiment the effective amount of sulfide reducer is a dose such that when administered the patient plasma reaches an $IC_{50}$ for the sulfide reducer. According to a further embodiment the biochemical sulfide is total sulfide and the elevated threshold level is 1.32 µM. According to a further embodiment the method further comprises determining a level of free sulfide in the plasma, and only diagnosing the patient with ADRD if both the level of free sulfide is normal and the level of the biochemical sulfide is at least an elevated threshold level for the biochemical sulfide. According to a further embodiment the normal level of free sulfide is less than 0.80 µM. According to a further embodiment the normal level of free sulfide is less than 0.70 µM.

The present invention relates to pharmaceutical compositions of a therapeutic (e.g., sulfide reducer), or a pharmaceutically acceptable salt, solvate, ester, amide, clathrate, stereoisomer, enantiomer, prodrug or analogs thereof, and use of these compositions for the treatment of ADRD.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In some embodiments, the condition is an ADRD.

In certain embodiments, the ADRD is mild to moderate ADRD.

In further embodiments, the ADRD is moderate to severe ADRD.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the ADRD.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., sulfide reducer, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., an ADRD). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIGS. 2A-2D are scatterplots of cognitive function, $H_2S$ and lesion volume outcomes. Strong relationships were observed between $H_2S$ metabolites (particularly acid labile and total sulfide) and both the cognitive outcome measure (FIG. 2A) and the measure of chronic microvascular disease (FIG. 2B). FIG. 2C is a scatterplot showing the strong relationship between cognitive function and microvascular disease. FIG. 2D is a model of mediation analysis (left) and mediation analysis results (right). Total sulfide mediated the relationship between the measure of cognitive function and the measure of chronic microvascular disease. Control is indicated by a solid black circle and ADRD is indicated by a white circle with black outline.

FIG. 3A reports ROC of free sulfide, FIG. 3B shows ROC for acid labile sulfide, FIG. 3C illustrates ROC for bound sulfide, and FIG. 3D shows ROC for total sulfide. Area=area under the curve.

FIG. 4A is a decision tree showing total sulfide as the most effective classifier, with a cut off value of 1.64 µM $H_2S$; AD: Alzheimer's Disease related dementia; CT: control. FIG. 4B is a classifier performance metrics for the tree classifier according to their ability to predict diagnosis (see methods for description of classifier metrics). A single dimension was chosen (Total Sulfide) by the classifier despite the number of candidate dimensions. The inventors also ran the analysis using only the records containing MRI data for comparison (MRI-only). The "All" and "Total $H_2S$" facets have duplicated accuracy statistics because in both of these, the same decision tree was generated. The inventors used several measures to classify the accuracy of the classifier. Accuracy describes the probability that the classifier arrives at a correct prediction. Sensitivity describes the probability of correctly predicting a positive condition. Specificity describes the probability of correctly predicting a negative condition. False negative rate and false positive rate indicate the failure of the classifier to correctly categorize positive or negative conditions. Positive predictive value and Negative predictive value represent the reliability of a positive or negative condition respectively. False discovery rate and Fake omission rate represent the probability that the respective predicted condition does not represent the actual condition.

FIG. 7 is a table showing demographic data for the total sample (Total) and the MRI subgroups (MM). The inventors' total sample was predominantly female (ADRD=86.7% vs. Control=85.7%). About half of the participants were African American (AA; ADRD=53.8% and Control=52.7%) and the other half were white. Proportions were similar for the Mill subgroups. *$p<0.001$ for ADRD vs control.

FIGS. 8A and 8B are a single table split over two sheets showing a correlation matrix of demographic, cognitive, MM and $H_2S$ variables. *$p<0.05$, **$p<0.01$.

DETAILED DESCRIPTION

Figure 1:
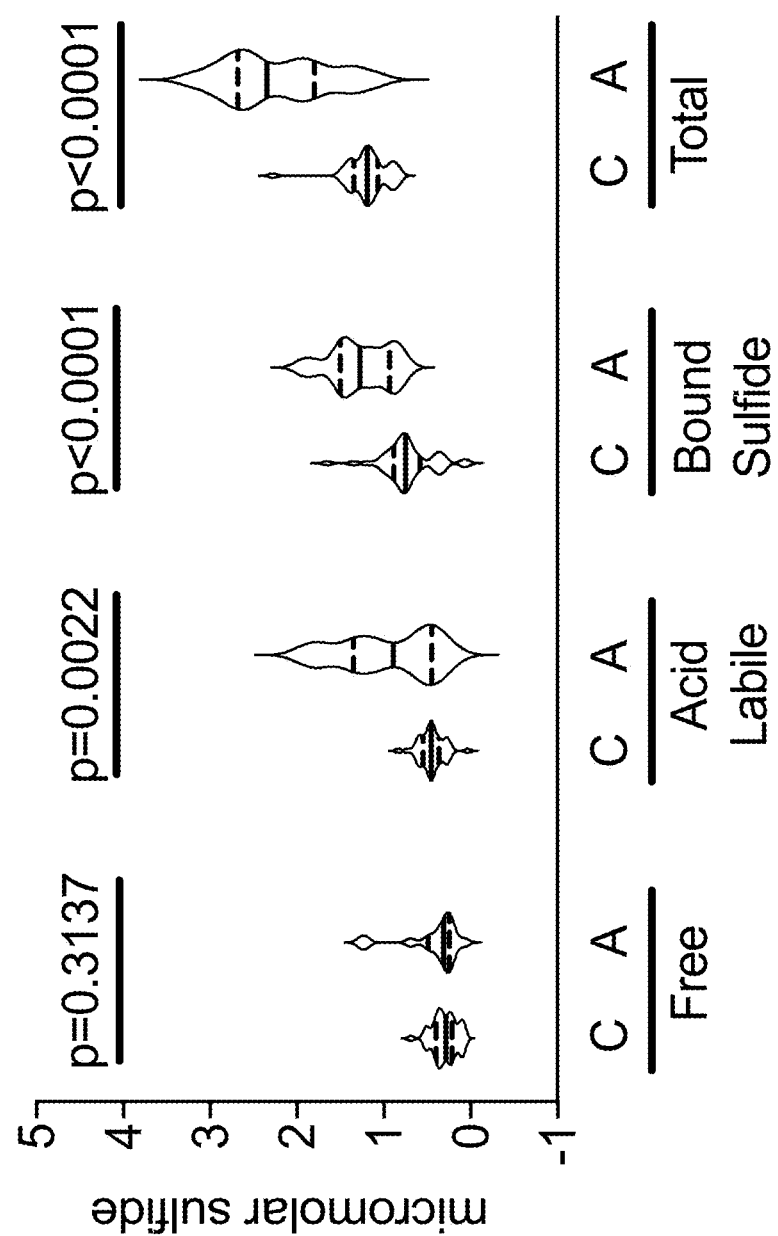
FIG. 1 is a violin plot of the median and distribution densities of plasma $H_2S$ metabolite measures in control (C) and Alzheimer's Disease related dementia (A) participants. The violin plot is a nonparametric representation of all data points. The solid line is the group median, while the width of each plot represents subject density. Dashed lines indicate the interquartile range.
Figure 3A:
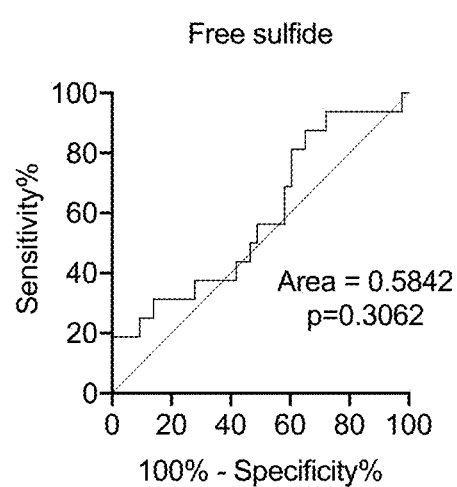
FIGS. 3A-3D are receiver-operating characteristic (ROC) curve analysis demonstrating that $H_2S$ metabolites are indicators of ADRD.
Figure 3B:
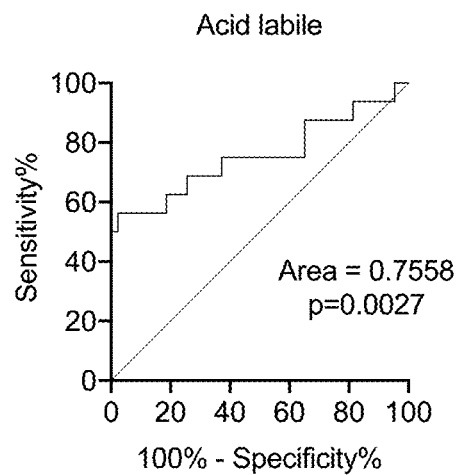
Figure 3C:
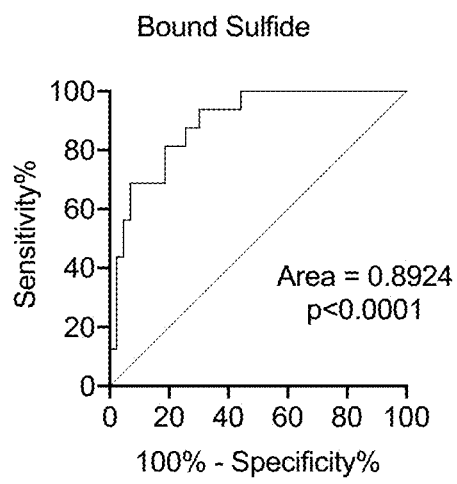
Figure 3D:
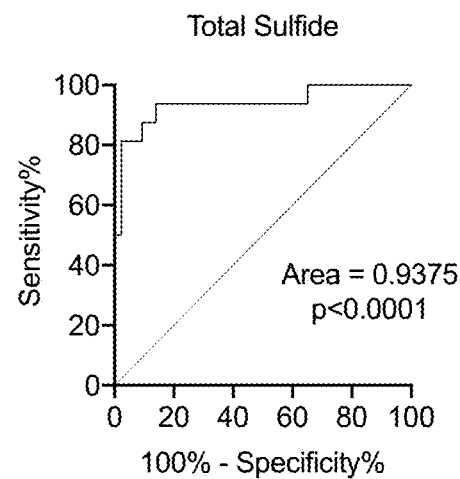

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-8B, a brief description concerning the various components of the present invention will now be briefly discussed.

Because Alzheimer's disease (AD) is the most common form of age-related neurological disability, identifying and treating its underlying causes is a critical health challenge. The etiology of AD is complex and multifactorial. While the amyloid cascade hypothesis suggests that accumulation of amyloid 'plaques' and phosphorylated-Tau (p-Tau) tangles play mechanistic roles in AD, therapies targeting suppression of these factors have not yet proven clinically effective. Furthermore, amyloid 'plaques' and p-Tau are also present in non-AD forms of neurodegeneration, thus it is not surprising that diagnostic strategies relying on amyloid and p-Tau have shown mixed results. Recently, there has been progress made in identifying isoforms of p-Tau that may differentiate AD from other tauopathies, although it remains to be seen if therapeutic targeting of specific p-Tau isoforms, rather than general overall p-Tau, will more successfully modify disease, or if these isoforms will prove most useful for diagnosis.

The inventors postulate that there is a link between cerebrovascular disease and dementia. Furthermore, the incidence of both dementia and stroke appears to be increasing in tandem worldwide, reflecting socioeconomic status and its influence on largely modifiable vascular risk factors. Cerebrovascular dysfunction occurs early in ADRD, and may allow for an earlier diagnostic marker and a more fruitful therapeutic target. In ADRD, vascular dysfunction can drive inflammation which weakens the blood brain barrier (BBB), potentially initiating a cascade of pathophysiologies leading to AD progression. Specifically, disturbances in BBB integrity may set off a cascade of events including excitotoxic calcium signaling and metabolic stresses which progressively damage brain structure/function and culminate in amyloid 'plaques' and p-Tau tangles. Consequently, AD and vascular dementia appear to be overlapping and potentially linked clinical phenomena, rather than discrete disease categories. Here, the inventors hypothesize that plasma hydrogen sulfide ($H_2S$) represents a novel vascular biomarker whose concentration is tightly associated with cognitive dysfunction and disease activity in Alzheimer's disease and related dementias (ADRD).

1.1 Hydrogen Sulfide and its Metabolites in Vascular Dysfunction and Neuropathology $H_2S$ and its metabolites plays a role in the regulation of both vascular and neuronal homeostasis. Plasma $H_2S$ and its metabolites are vascular disease blood biomarkers, and imbalances in $H_2S$ metabolism exist in the vascular compartment during several disease states. In the brain, $H_2S$ acts as a neurotransmitter/second messenger produced following nerve excitation, and modulates NMDA receptors during long term potentiation for memory consolidation. Several cell types within the brain and its vasculature generate $H_2S$ from cysteine. In the brain parenchyma, $H_2S$ is produced by the enzyme cystathionine BETA-synthase (CBS), while cystathionine GAMMA-lyase (CSE) generates $H_2S$ derived from cerebral microvessels. Additionally, three biochemical forms of reactive sulfur pools exist: free $H_2S$ (or free sulfide), acid-labile sulfide (e.g., iron-sulfur clusters) and bound sulfane sulfur (or bound sulfide) (e.g., persulfides, polysulfides). The total of the three pools is called the total sulfide or total labile sulfide.

Figures 4A, 4B:
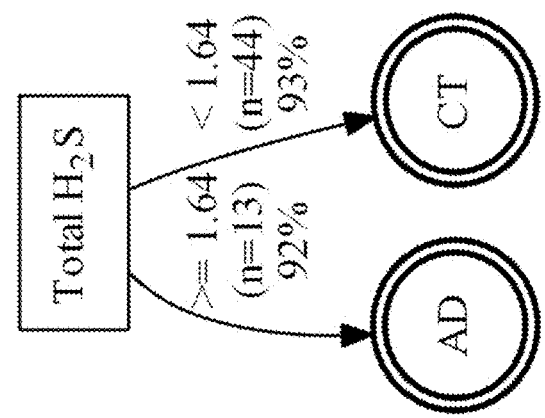
FIGS. 4A and 4B is a Tree Classifier.

The neurovascular actions of $H_2S$ and its metabolites in disease are complex, with both protective and damaging effects, including defensive roles for $H_2S$ in preserving normal brain vasomotion, and cognitive function in experimental models of dementia. Conversely, $H_2S$ and its metabolites contribute to neurological stress and vascular dysfunction, a deleterious role consistent with the inventors' current findings. Here, for the first time the inventors have shown that plasma $H_2S$ and $H_2S$ metabolites are elevated in ADRD (FIG. 1), and levels are associated with both cognitive dysfunction and neuroimaging evidence of microvascular disease (FIGS. 2A-2D). These findings indicate that the link between $H_2S$ imbalance and ADRD may be due, at least in part, to microvascular dysfunction. When the inventors tested this possibility using mediation analysis (FIG. 2D), results indicated that $H_2S$ drove half of the relationship between cognitive dysfunction and microvascular disease. In addition, $H_2S$ and its metabolites had significant ADRD diagnostic ability (FIGS. 3A-3D), and classifier analysis revealed that total plasma sulfide burden was the best indicator of ADRD. A threshold of 1.64 µM plasma $H_2S$ yielded a classification accuracy=0.930 and a sensitivity of 0.80 (FIGS. 4A-4B). It is noteworthy that plasma $H_2S$ alone was a powerful discriminator between ADRD and controls, and that a combined approach, including imaging and demographic data, did not further improve the sensitivity and specificity of the inventors' decision tree classification model.

The apparent contradictory findings for the role for $H_2S$ in brain-related pathologies are consistent with literature on other gasotransmitters such as nitric oxide (NO), where in some pathologies excess NO has been shown to be deleterious, while in others decreased NO bioavailability has been reported. The fact that both too little and too much $H_2S$ can be detrimental to brain health may represent a neuroprotective system that breaks down under pathological conditions. Similarly, administration of sodium hydrosulfide, an $H_2S$ donor actually increased infarct volume, while sulfide inhibitors limited size of infarct.

The inventors conclude, based on their studies, that $H_2S$ becomes dysregulated in ADRD, where vascular and cognitive functions are intimately linked. One possible mechanism through which $H_2S$ levels are elevated is suggested by a hypothesis in which cerebral hypoxia contributes to AD/ADRD pathogenesis. Because hypoxia and ischemia are potent inducers of CSE expression and function, age-related vascular deficits in brain oxygenation implicate CSE activity in neuronal dysfunction, particularly in areas of the brain where oxygenation is compromised. Furthermore, hypertension and disturbances in cerebrovascular flow, often seen in ADRD may enhance CSE expression and activity and increase 'bound' polysulfide pools. It is interesting to speculate that the recent successes of hyperbaric oxygenation on AD might be consistent with this model, where relief from hypoxia may also influence sulfide 'burden'. Each of these scenarios are consistent with oxygenation abnormalities creating $H_2S$ links to a vascular dysregulation, and anticipate associations between the vascular dysfunction observed in the brain and alterations in circulating $H_2S$ metabolites in ADRD.

Figure 5:
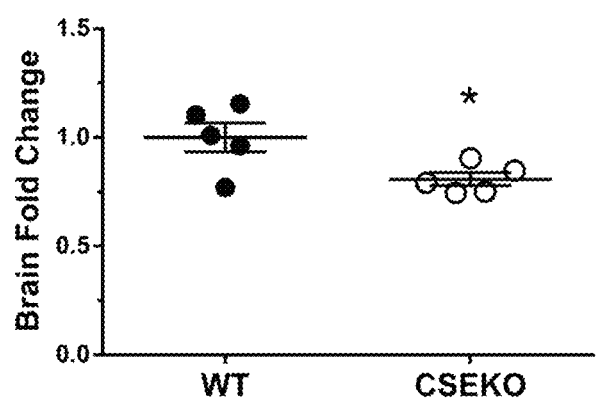
FIG. 5 shows CSEKO mice exhibit reduced vascular permeability. Sodium fluorescein permeability was significantly reduced in the brains (top) and lungs (bottom) of CSEKO mice compared to WT controls (*significant $p<0.05$, student's t-test, n=5/group).
Figure 5:
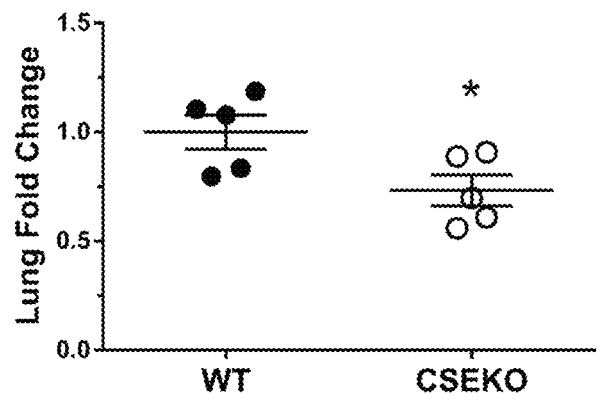

1.2 Pathways through which Hydrogen Sulfide Disrupts Brain Microvasculature: The inventors queried how might AD disease activity, cognitive dysfunction and neuroimaging be related to sulfides. The answer may lie in early, 'silent' BBB disturbances driven by abnormal $H_2S$ homeostasis. The inventors have investigated several gasotransmitters including $H_2S$, NO and their metabolites as contributors to vascular endothelial barrier failure. The inventors showed that exogenous polysulfide donors (not free sulfide donors) act on endothelial junctions to depress vascular barrier in vitro. The inventors have evidence that such a damaging role for $H_2S$ metabolites also applies to the BBB, where barrier disruption early after stroke is mediated by $H_2S$ species. Specifically, the inventors' studies on the impact of $H_2S$ on the brain vasculature revealed a role for CSE-derived $H_2S$ metabolites in ischemic stroke induced vasodilation/hyperemic response and barrier permeability early during reperfusion. It should be noted that polysulfides can be generated endogenously both by the oxidation of $H_2S$, and directly from CSE. Therefore, the inventors examined the role of CSE in basal vascular integrity. Using CSE-deficient mice (CSEKO), the inventors observed a significant reduction in small solute (sodium fluorescein) permeability in the brain, indicating that the barrier function was enhanced in the absence of CSE. This effect was not specific to the brain, as the inventors saw a similar response in the lungs (FIG. 5). This multi-organ finding, along with the fact that CSE is primarily found in the vasculature, represents a first step in proving the inventors' hypothesis that a vascular source of CSE-derived $H_2S$ is responsible for the imbalance in $H_2S$ homeostasis in ADRD patients.

Figure 6:
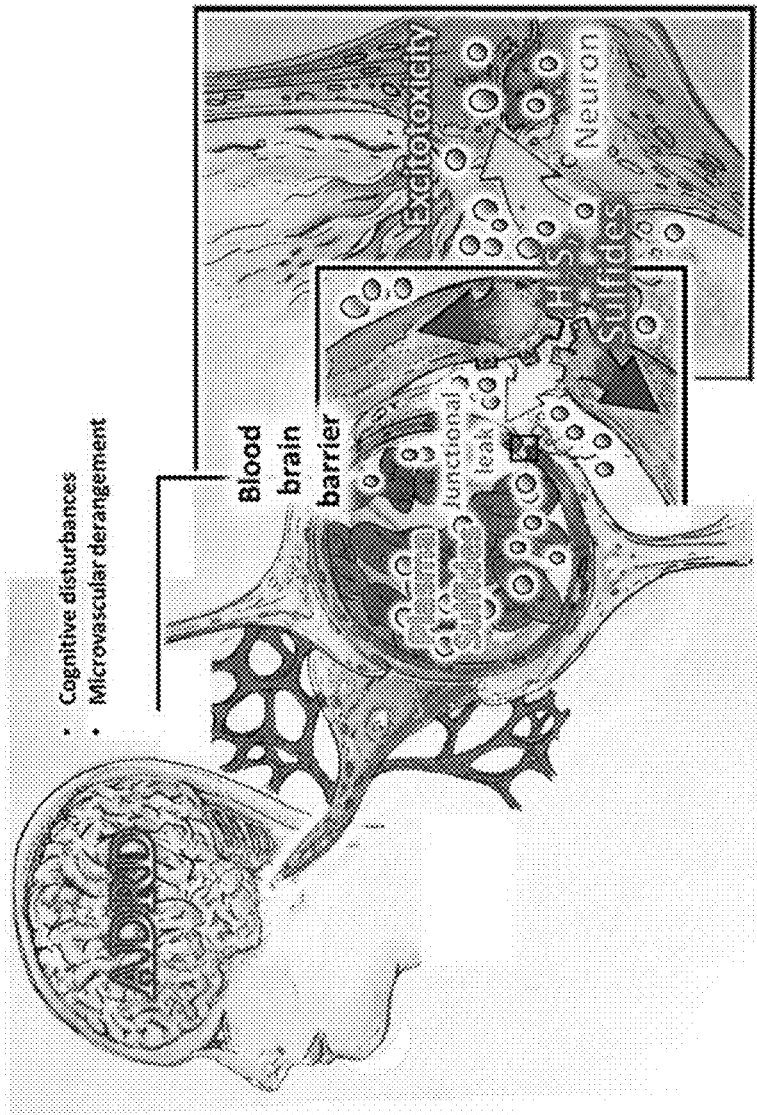
FIG. 6 is a scheme for sulfide dysregulation in ADRD. In ADRD, increased accumulation of sulfides, measured in plasma, may reflect increased formation of $H_2S$ metabolites produced in the vascular compartment. Several sulfide species are known to impair blood brain barrier leading to persistent excitotoxic stress and subsequent destructive changes in brain microvascular structure and cognitive function seen in ADRD.

The inventors' findings are consistent with a scheme where elevated levels of $H_2S$ and its metabolites drive barrier disturbances, which underlie excitotoxic stress and cognitive injury, particularly in AD. In ADRD, disturbances in brain endothelial barrier function can flood the brain interstitium with toxic neurotransmitters, immune components and iron, each potentially able to trigger a progressive, and calcium-dependent, excitotoxicity (FIG. 6). Over the course of years, these changes could lead to structural and functional derangement seen in longstanding ADRD, the duration that manifests cognitive symptoms. The inventors' findings reveal that sulfide stress appears to represent an important indicator of ADRD disease activity which links brain vascular disturbance to cognitive dysfunction, and provides valuable novel diagnostic, prognostic and mechanistic insights into ADRD.

1.3 Limitations: The inventors recognize that this study is limited by participant ADRD diagnosis that is unconfirmed by autopsy. However, even with the possible heterogeneity of the inventors' dementia group, the $H_2S$ discriminatory power was exceptionally high. Despite such limitations, these small groups were a highly studied cohort of individuals and show a remarkable and mathematically compelling relationship between $H_2S$ and cognitive dysfunction, indicating that larger studies would likely recapitulate these findings. At this point, there are a number of questions that remain unanswered due to the limited number of participants, including examination of relevant disease subgroups such as comorbidity, sex or raced based cohorts. Nonetheless, the inventors' findings that $H_2S$ metabolites provide higher diagnostic performance than even blood BETA-amyloid secondary structures, despite the very limited number of individuals, strongly supports pursuit of this approach.

1.4 Future directions for Hydrogen Sulfide as a Biomarker for ADRD: The inventors' initial biomarker studies are highly promising. The association between blood $H_2S$ levels and microvascular disease suggests that increased generation of $H_2S$ from CSE, abundant in cerebral microvessels, may drive ADRD progression. The inventors' results showed that total sulfide mediated the relationship between cognitive outcomes and microvascular dysfunction, supporting a causal role for $H_2S$ dysregulation in ADRD. The inventors' study indicates that at least some of these $H_2S$ metabolites, such as oxidized $H_2S$, likely accumulate in the circulation with disastrous consequences. The fact that powerful group discrimination could be obtained using only a single plasma analyte is remarkable in the ADRD field. These findings suggest further steps are warranted to verify biomarker sensitivity and specificity.

The inventors' work also anticipates longitudinal studies for the evaluation of early detection and progression monitoring. The linear nature of the relationships among cognitive and lesion volume measures with total sulfide, as well as acid-labile and bound sulfide pools evidence that $H_2S$ metabolites reflect disease progression and thus have prognostic value. Based on the inventors' observations, modulation of plasma sulfides also represents a therapeutic opportunity in ADRD. If further studies sustain the inventors' and modifiable risk factors do contribute to ADRD progression, earlier intervention in such 'at-risk' individuals would limit or prevent inevitable progression into clinical ADRD. Because blood sampling remains the easiest, most repeatable and inexpensive method of evaluating biospecimens, reliable blood-based diagnostics for ADRD, as described here, would have an enormous impact in combatting ADRD.

CONSOLIDATED RESULTS AND STUDY DESIGN: Hydrogen Sulfide and its metabolites in ADRD and associated cognitive impairment: The physiology of $H_2S$ and $H_2S$ metabolites in ADRD and related neuropathology is not well understood in the field. Since the most accessible pools of $H_2S$ are in the circulation, the inventors' first step was to determine if plasma levels of $H_2S$ and its metabolites were different in people with and without ADRD. The inventors enrolled 15 participants with ADRD and 42 controls for cognitive and blood testing, and, of these, 12 ADRD and 19 control participants also had MIll (FIG. 7). The inventors found that total $H_2S$ levels increased with ADRD, and that this increase was primarily due to elevations in both acid-labile and bound sulfide pools, not free sulfide (FIG. 1). This finding is in contrast to the inventors' observations from cardiovascular disease, where patients suffering such disease show a decline in plasma total, bound and acid-labile $H_2S$ levels, thus suggesting a disease mechanism that is unique to the brain. Furthermore, the inventors' findings disagree with the only previous study on $H_2S$ in human AD and vascular dementia, which reported decreased $H_2S$ levels in plasma for AD. $H_2S$ supplementation has also been shown to be protective in animal models of AD. These results are apparently conflicting with the inventors' experimental data, underlying the complexity of this chemical. Further, the inventors do not know whether some of these conflicting findings relate to the populations studied or the methods used to measure $H_2S$. The inventors used an advanced method of $H_2S$ measurement developed by the inventors' group, and which was designed to address limitations of the method used by many others. These contrasting findings may also relate to discrepancies between results from murine models of AD and human ADRD.

More specifically, cardiovascular disease risk factors such as diabetes, hyperhomocysteinemia and hypertension are known as risk factors for Alzheimer's disease and related dementias (ADRD). The inventors have previously shown that patients with cardiovascular disease have decreased levels of total sulfide, in particular free $H_2S$, in plasma. Free $H_2S$ is often considered to be a vasoprotective antioxidant, therefore, based on current understandings and teachings in the art, the inventors hypothesized that free $H_2S$ levels would be decreased in plasma of ADRD patients.

However, the inventors' findings in this application disproved the inventors' hypothesis and instead showed that ADRD is associated with elevated levels of total $H_2S$, specifically bound and acid-labile sulfide pools, while free $H_2S$ levels were unchanged. This is in contrast to the only previous study on $H_2S$ in human AD and vascular dementia that reported decreased $H_2S$ levels in plasma. While these apparently conflicting results are consistent with a dual role for $H_2S$ where both deficient and excessive levels are pathological, the inventors' findings also indicate that a redistribution between $H_2S$ pools may be a critical determinant in the pathological consequences, which no previous studies have measured. It is also possible some of these conflicting findings relate to the populations studied or the methods used to measure $H_2S$. To address limitations of the analytical method used by many other groups, the inventors' applied an advanced, non-routine, non-conventional, and precise method developed by our group to measure these $H_2S$ species. Several findings by other groups (including a very recent study by Giovinazzo et al., 2021) contradicting the inventors' findings, suggest that $H_2S$ donors are beneficial in ADRD. However, these other results were found in murine models of ADRD, and the inventors have preliminary data that shows that some murine models do not apparently reflect changes in plasma $H_2S$ observed in human ADRD.

Of importance from a mechanistic perspective was whether circulating $H_2S$ metabolite levels correlated with anatomical and/or vascular impairments. To better understand the relative roles for $H_2S$ in these two interrelated components of ADRD, the inventors used typical diagnostic indices, and correlated them with plasma $H_2S$ levels. Mill has been widely applied to identify cerebral ventricular and hippocampal volumes as a measure of AD status. As expected, the inventors' ADRD population showed decreased hippocampal and increased ventricular volumes. While neither of these indices correlated with levels of $H_2S$ or individual sulfide pools, there was a clear, inverse relationship between total brain volume and $H_2S$ levels (FIGS. 8A and 8B). In addition, the MRI based microvascular lesion outcome measure was strongly correlated with both acid-labile and total $H_2S$ (FIGS. 8A and 8B).

Of primary importance from a clinical perspective was quantifying the cognitive impairment that characterizes ADRD. Using the Alzheimer's disease Assessment Scale (ADAS-Cog) score as a measurement of cognitive function, the inventors' finding of higher ADAS-Cog scores in ADRD link cognitive dysfunction with higher $H_2S$ levels in the plasma. In fact, the ADAS-Cog correlated very tightly not only with total $H_2S$, but also with both acid-labile and bound sulfide pools. To examine the causal relationship among cognitive function, microvascular lesion volume and $H_2S$ the inventors further employed mediation analysis. Specifically, the inventors examined the contribution of $H_2S$ to the relationship between cognitive function and microvascular disease. Total $H_2S$ was found to drive half of the effect of lesion volume on cognitive function (FIG. 2D). This finding indicates that $H_2S$ metabolites may be mechanistically significant as a contributor to ADRD. Importantly, these findings are consistent with cognitive and structural disturbances related to sulfides that originate in the vascular space and act to disrupt vascular homeostasis, leading to downstream neurodegeneration.

Sensitivity and Specificity of Sulfides in ADRD: ADRD diagnostic tools remain somewhat unreliable and differ in their specificity and sensitivity. The current mainstay of AD diagnosis, the ADAS-cog score has good sensitivity and specificity at 90.09% and 85.88% respectively. While widely applied, ADAS-cog requires trained operators, is time-consuming and is subject to variability based on patient performance. Hippocampal and ventricular changes on Mill also predict disease activity. Plasma BETA-amyloid has also been widely studied as an AD biomarker; its use in receiver operator characteristic (ROC) curve analysis discriminated AD patients from controls with a specificity/sensitivity of 91% and 71% respectively (AUC=0.80). Overall, its diagnostic accuracy was good, but not ideal (86%). The problem with such approaches is that AD diagnosis still remains probabilistic, with the most definitive confirmation only available at autopsy. Low diagnostic accuracy in AD may be related to its complex nature, long course and variable etiopathogenesis. Thus, the most accurate approach may be a biomarker panel. Although the inventors found significant diagnostic performance for acid-labile, bound, and total sulfide (FIGS. 3A-3D), greater discriminative ability was noted with total sulfide (AUC=0.94, 95% confidence interval: 0.92 to 1.000; panel 3D).

In order to maximize the discriminative power of the inventors' blood, Mill and behavioral data, the inventors performed classification analysis to create a decision tree.

A decision tree analysis yields a graphic representation of alternative solutions based on probability analysis. The inventors included all Mill and $H_2S$ variables as indicators of ADRD. This analysis provided a decision tree that had a single level consisting of total sulfide (FIG. 4A). The tree had an accuracy of 93.0%, a sensitivity of 80%, a positive predictive value of 92.3% and a negative predictive value of 93.2% (FIG. 4B). These findings indicate that total $H_2S$ alone accurately reflects the contribution of brain volume, microvascular and $H_2S$ metabolite abnormalities to cognitive disturbance in ADRD. While it remains to be seen if the addition of BETA-amyloid or p-Tau outcomes can improve diagnostic power of total plasma $H_2S$, the inventors' findings reveal that $H_2S$, when used alone, is a very powerful predictor of ADRD.

DETAILED METHODS AND RESULTS: Methodological and Technical Specifics of Human Studies: Subjects: Written informed consent was obtained according to the policy of the institutional review board of Louisiana State University Health Sciences Center, Shreveport. The inventors studied 16 individuals who met the criteria for 'ADRD' (ADAS-cog score>17 or clinical diagnosis of AD (1 subject, ADAS-cog score=10)) and 42 age-similar controls. Inclusion criteria were age >50 years (mean 67.8 yrs) with English as their primary language. A subset of participants (n=12 ADRD, 19 controls) met inclusion/exclusion criteria and underwent MM. Cognitive evaluation (ADAS-cog) tests, and blood draws were performed at the same visit, with Mill performed on average 42 days after neuropsychological testing.

Cognitive Assessments: Cognitive status was evaluated using the MMSE. Dementia was defined as an Alzheimer's disease Assessment Scale, or ADAS-cog score of >17. The total session duration was 2-4 hours.

Hydrogen Sulfide Analysis: Blood was collected in lithium-heparin vacutainer tubes and processed within 15 minutes. Samples were centrifuged at 1400 RCF for 4 minutes. Plasma was combined in a 5:1 ratio of plasma to stabilization buffer (degassed 100 mM Tris-HCl buffer, pH 9.5, 0.1 mM diethylene triamine pentaacetic acid), quickly frozen and stored in liquid nitrogen until analysis. The sulfide pools were isolated according to analytical reversed-phase high pressure liquid chromatograph (RP-HPLC) procedures previously established in the inventors' lab. Derivatization of sulfide with excess MBB (monobromobiamine) was performed under specific reaction conditions for all three pools (free, acid-labile, and bound). Each evaluation was performed in triplicate. This protocol is described by Shen, et al., Measurement of $H_2S$ In Vivo and In Vitro by the Monobromobimane Method. Methods in Enzymology. 554C. 31-45 DOI: 10.1016/bs.mie.2014.11.039 (2015), such document incorporated by reference.

Briefly, the protocol involves selective liberation, trapping and derivatization of labile $H_2S$. The free $H_2S$ was measured employing excess MBB under alkaline, 1% oxygen, and trace-metal-free conditions followed by RP-HPLC and fluorescence detection of the sulfide dibimane product. Acid-labile $H_2S$ was released by incubating the sample in an acidic solution (e.g., pH 2.6, 100 mM phosphate buffer with 0.1 mM DTPA) and measured along with free $H_2S$ in an enclosed system to contain the volatilized $H_2S$. Volatilized and free $H_2S$ was then trapped in an alkaline solution (e.g., 100 mM Tris-HCl, pH 9.5, 0.1 mM DTPA), and then reacted with excess monobromobimane to form the stable fluorimetric product sulfide-dibimane. In a separate sample aliquot, the total labile sulfide, including the contribution of bound sulfane sulfur pool, the acid-labile pool, and free $H_2S$, was measured by incubating the sample with the reducing agent TCEP (Tris(2-carboxyethyl)phosphine hydrochloride), to reduce disulfide bonds in an acid solution (e.g., in 100 mM phosphate buffer, pH 2.6, 0.1 mM DTPA), and after removing the solution, the volatilized $H_2S$ was trapped using alkaline buffer with MBB as described above.

The amount of sulfide in the three individual sulfide pools was then determined by the following. The amount of free $H_2S$ is directly measured. The amount of acid-labile sulfide is the difference between the measurement of acid-labile+free $H_2S$ and the measurement of free $H_2S$. Finally, the amount of bound sulfane sulfur is the difference in the measurement of total sulfide and the measurement of acid-labile+free $H_2S$.

Brain Imaging: Participants underwent a 1 h MRI on a 3T Philips Ingenia™ scanner. During image acquisition, subjects were instructed to keep their eyes closed and move as little as possible. Scans included a 3D MP-RAGE (FOV 250×250×181 mm, Acq Matrix: 228×227 mm, Recon Matrix:240 mm, TE=3400, TR=7400), and a 3D fluid-attenuated inversion recovery (FLAIR) images (FOV 270×270×168 mm, Acq Voxel: 1.13×1.13×1.12 mm, Recon Voxel: 0.56×0.56×0.56 mm, TE=328, TR=4800, TI=1650). Diffusion, pCASL and T2*GRE images were also collected but were not included in this analysis.

Image Processing: For volume measurement, T1-weighted images were subjected to automated cortical reconstruction implemented in version 6.0 of the Free-Surfer™ image analysis suite (surfer.nmr.mgh.harvard.edu). Images were then processed for motion correction, intensity normalization and acquisition artifacts. Images were transformed and stripped of non-brain tissue for normalization into Talariach space for morphometric estimations. Images underwent cortical surface parcellation and subcortical volume-based segmentation. Estimates of cortical and hippocampal volume were obtained using this automated algorithm of subcortical segmentation. Data were visually inspected at key steps for errors preceding the analyses.

FLAIR lesion volume was calculated using the lesion growth algorithm as implemented in the LST open-source toolbox version 3.0.0 for SPM. The inventors' computations were completed with MATLAB R2019a and SPM12. T1 images were co-registered to the FLAIR image and lesion maps were calculated based on a user-determined threshold (kappa, 0.3). Lesion volume outcome is reported as a percentage of lesion volume over total brain volume.

Statistical Analysis: All variables were evaluated across disease groups using multivariate analysis of variance (MANOVA). Pearson correlation was used to evaluate the relationship between $H_2S$ metabolites and cognitive and imaging outcome measures. These analyses were performed using SPSS version 26. The inventors also performed ROC analysis to illustrate the ability of $H_2S$ metabolites to distinguish ADRD and control groups using GraphPad Prism v8.4.2 (GraphPad Software, San Diego, Calif. USA). An alpha level of 0.05 was used to determine statistical significance. Outliers were defined as any data point that was >3 SD from the group mean.

To generate decision trees, the inventors used the rpart algorithm (https://cran.r-project.org/web/packages/rpart/rpart.pdf), a regression and classification tree induction algorithm that included the following variables: diagnosis; age; years of education; % hippocampal, lesion and ventricle volume; as well as free, acid-labile, bound and total $H_2S$. The inventors used 10-fold cross-validation to reduce the chances of model overfit. In addition, the inventors produced a decision tree based on the $H_2S$ variables alone. Because the control group was larger than the ADRD group the decision tree analysis was performed again using the MRI subgroup.

The inventors also used mediation analysis to test the hypothesis that the effect of a predictor variable (% lesion volume) on an outcome (ADAS score) operated fully or in part through an intervening mediator (e.g., total sulfide). Mediation analysis was performed using the PROCESS SPSS macro provided by Hayes and Preacher to perform such analysis.

Sodium Fluorescein (Na—F) extravasation in Mice: In vivo endothelial barrier function was evaluated in C57BL/6 J wild-type (WT) and CSEKO mice using Na—F (Sigma, Cat. #F-6377) extravasation. All procedures for handling animals complied with the Guide for Care and Use of Laboratory Animals and were approved by the ACUC Committee of LSU Health Sciences Center-Shreveport. All animals were cared for according to the National Institutes of Health guidelines for the care and use of laboratory animals. Briefly, mice under isoflurane anesthesia were injected with 5% Na—F in saline via tail vein (0.4 mg/kg) and were humanely euthanized after 20 minutes. Blood was collected from inferior vena cava, and the vasculature was thoroughly perfused via the heart with PBS. The brain and lungs were dissected and homogenized in PBS (1 ul/mg) using a tissue homogenizer (Thomas scientific, Swedesboro, N.J.). Lysates were mixed with equal volumes of 50% trichloroacetic acid (TCA) (Sigma, Cat #T-6399), and plasma was mixed with 9 volumes of 20% TCA. All samples were held at 4° C. overnight to precipitate protein and were then centrifuged at 12,000 g for 20 minutes. Two volumes of 1× Tris-borate-EDTA buffer (Sigma, T4415) were added to every volume of supernatant, and pH adjusted to 7.5-8.5 using NaOH. Two-fold dilutions were prepared for each sample in Tris-borate-EDTA buffer and fluorescence measured at 485/538 nm and compared to known Na—F standards. The amount of Na—F in samples was calculated in samples where fluorescence was in the linear range. Final results were normalized to plasma and presented in fold changes.

Detailed Results: Participant Characteristics: Participant characteristics are shown in the table of FIG. 7. One outlier ADRD subject was excluded based on MRI; therefore, final sample sizes were 15 ADRD and 42 controls. The inventors had an MRI subset of 12 ADRD and 19 controls after one ADRD subject was excluded due to contraindications for MRI and two because of an appointment that was canceled due to COVID-19 closures. There were no significant differences between ADRD and control subjects for age ($F(1, 55)=0.12$, $p=0.73$) or years of education ($F(1,55)=2.54$, $p=0.12$). The ADRD group had significantly higher ADAS-cog scores ($F(1,55)=93.75$, $p<0.001$), indicating poorer cognitive performance.

Group differences in $H_2S$ Metabolites Imaging and Outcomes: The ADRD group had significantly increased levels of $H_2S$ metabolites (FIG. 1). Acid-labile ($F(1,55)=25.99$, $p<0.0022$), bound ($F(1,55)=29.69$, $p<0.0001$), and total sulfide ($F(1,55)=79.12$, $p<0.0001$) were all elevated in the dementia group compared to controls.

The inventors found differences across groups in MRI outcome measures. Total brain volume was significantly reduced in ADRD (939(105) mm$^3$) compared to controls (1029(101) mm$^3$; $F(1,30)=5.73$, $p=0.023$). The inventors therefore normalized hippocampal, total gray and white matter, FLAIR lesion and ventricular volumes by dividing these measures by total volume to obtain a percentage. The ADRD group (Mean(SD)=0.67 (0.073)%) had significantly reduced % hippocampal volume compared to controls (0.72 (0.053)%; $F(1, 30)=5.89$, $p=0.022$) as well as increased ventricle size (ADRD=3.61 (1.9)%, Control=2.12 (1.6)%; $F(1,30)=7.360$, $p=0.011$). There were no significant differences across groups for % gray matter (ADRD=54.68 (2.96)%, Control=55.99 (1.48)%; $F(1,30)=2.65$, $p=0.116$) nor % white matter volume (ADRD=42.49 (2.81)%, Control=41.26 (1.43)%; $F(1,30)=2.61$, $p=0.114$). Percent FLAIR lesion volume was significantly larger in the ADRD group (0.76 (0.72)%) versus controls (0.17 (0.16)%; $F(1, 30)=11.99$, $p=0.002$).

ROC Curve Analysis of $H_2S$ Metabolites: Receiver-operating characteristic (ROC) curve analysis revealed significant diagnostic performance for acid-labile, bound, and total sulfide (FIGS. 3A-3D). Free sulfide ROC curve analysis results were not statistically significant (area under the curve AUC=0.58; 95% confidence interval: 0.42 to 0.75) (panel 3A). Discriminative capability for acid-labile was significant with AUC=0.76, 95% confidence interval: 0.59 to 0.92 (panel 3B). However, much higher discriminative ability was noted with bound (AUC=0.89, 95% confidence interval: 0.80 to 0.97) (panel 3C) and total sulfide (AUC=0.94, 95% confidence interval: 0.92 to 1.000) (panel 3D), respectively.

Correlation, Decision Tree and Mediation Analysis: Correlation analysis revealed a significant relationship between $H_2S$ metabolites and cognitive function (FIGS. 2A-2D and FIGS. 8A and 8B). ADAS-cog score was significantly positively correlated with acid-labile (456)=0.596, $p<0.0001$) and bound sulfane sulfur (r(56)=0.436, $p=0.001$), as well as total sulfide pools (456)=0.681, $p<0.0001$) (FIGS. 2A, 8A and 8B) indicating that poorer cognitive performance was associated with higher metabolite levels. FLAIR lesion volume was significantly correlated with ADAS-cog score (r(30)=0.687, $p<0.0001$) (FIGS. 8A and 8B). Lesion volume was also significantly positively correlated with acid-labile (430)=0.588, $p<0.0001$) and total sulfide (430) =0.452, $p<0.011$) (FIG. 2B), indicating that greater lesion volume was associated with higher sulfide metabolite levels. Importantly, neither ADAS-cog nor lesion volume were correlated with free sulfide (FIGS. 2A-2D and 8A and 8B).

Classification analysis using all variables (12 variables including demographic, MRI and $H_2S$ metabolites) provided a decision tree that had a single level consisting of total sulfide (FIG. 4A). The tree had an accuracy of 93.0%, a sensitivity of 80%, a positive predictive value of 92.3% and a negative predictive value of 93.2% (FIG. 4B). Removing MRI variables yielded an identical result. Reducing the number of subjects to those who underwent MM in order to reduce oversampling of control subjects resulted in slightly reduced accuracy of 90.3%, a positive predictive value of 90.9% and a negative predictive value of 90% (FIG. 4B). Again, exclusion of the MRI variables did not change model performance.

Mediation analysis revealed that total $H_2S$ mediated the effect of lesion volume on cognitive function (FIG. 2C). First, linear regression results showed that the relationship between % FLAIR lesion volume and total $H_2S$ was significant (a', b=0.0036, SE=0.0013, p=0.0107). Second, the relationship between total sulfide and ADAS-cog score was significant (b', b=1523, SE=406, p=0.0008). Finally, lesion volume was a significant predictor of ADAS-cog score (c', b=11.2, SE=3.2, p=0.002). Using a bootstrap estimation approach with 5000 samples the inventors determined that the indirect coefficient was significant (b=638.4, SE=299.7, 95% CI=53.9-1268.4). The inventors' findings indicate partial mediation, with a large (49%) proportion of the effect of lesion volume on ADAS-cog score operating indirectly through total sulfide.

CSEKO mice exhibit reduced vascular permeability: Using Na—F solute permeation as a measure of vascular barrier function, the inventors found striking improvements in blood-brain barrier of CSEKO mice compared to WT controls (FIG. 5). Interestingly, these improvements in barrier were also seen in the lung and therefore appears to reflect a generalized improvement in vascular barrier, which is not limited to the central nervous system, produced by reduction in $H_2S$ and its metabolites. Mice with this phenotype also have significant reductions in circulating sulfide species. When taken together with the inventors' previous studies revealing that endothelial cells exposed to per- and polysulfides show significantly diminished solute barrier, these data show that an environmental sulfide burden predicts endothelial barrier function. Consequently, the finding that the inventors' ADRD subjects have significantly higher sulfides is consistent with the hypothesis that sulfides in the vascular compartment might drive BBB disturbances that contribute to the initiation and progression of cognitive disturbance. The inventors' finding that FLAIR signatures in ADRD are consistent with microvascular derangement also fit this 'sulfide' model (FIG. 6).

According to the inventors' classifier analysis, total plasma sulfide burden was the best indicator of ADRD. A threshold of 1.64 μM plasma total sulfide yielded a classification accuracy=0.930 and a sensitivity of 0.80 (FIG. 4 from paper). Therefore, based on the inventors' total experimentations, a diagnosis of ADRD would be made if the level of plasma total sulfide was at least 1.00 μM, more preferably at least 1.32 μM, and most preferably at least 1.64 μM. To differentiate from other confounding morbidities, the level of plasma total sulfide would preferably be no more than 4.20 μM, and more preferably no more than more 3.30 Additionally, or alternatively, a diagnosis of ADRD would be made if the level of plasma acid labile sulfide was at least 1.00 µM, and preferably be no more than 3.0 µM, and more preferably no more than more 2.50 µM. Additionally, or alternatively, a diagnosis of ADRD would be made if the level of plasma bound sulfide was at least 1.40 µM, and preferably be no more than 3.0 µM, and more preferably no more than more 2.50 µM. Additionally, a diagnosis of ADRD could require both an elevated total, acid labile, or bound sulfide level and additionally a normal free sulfide level. The normal free sulfide level would be preferably be no more than 0.80 µM, and more preferably no more than more 0.70 µM, and most preferably no more than more 0.60 µM.

It is widely thought that accuracy of diagnosis of ADRD can be improved upon using a broader panel of biomarkers that includes imaging measures, cognitive function parameters and plasma biomarkers. The inventors' findings showed that plasma total $H_2S$ alone was a powerful discriminator between ADRD and controls, and it is significant that a combined approach, including imaging and demographic data, did not further improve the sensitivity and specificity of the inventors' decision tree classification model. This is evidence that $H_2S$ is integral to the pathology of ADRD, and is not only be diagnostic but also contributes to the mechanisms underlying disease. This is further supported by the inventors' findings that microvascular disturbances in the brain are correlated with cognitive dysfunction (FIGS. 2A-2D); total sulfide and the acid-labile sulfide pool correlate with microvascular disturbances; and total sulfide mediates at least half of the relationship between microvascular disturbances and cognitive impairment. Given that cerebrovascular dysfunction precedes plaque development and cognitive dysfunction, the inventors' findings suggest disturbances in sulfide metabolism occur early in the disease (before outward symptom manifestations) and thus represent a therapeutic target for ADRD. Because earlier interventions in ADRD may improve outcomes and delay disease progression, use of sulfides as a prognostic approach would allow optimal distribution of resources to individuals who may be at 'higher risk' based on their sulfide status. Sulfide level as an indicator of risk would be highly useful for stratifying risk for clinicians and healthcare management.

Because elevated plasma sulfides appear pathogenic for ADRD, drug strategies which relieve an excess burden of sulfides in the brain or brain vasculature would be prophylactic or therapeutic in ADRD. One goal of this therapy could be to manipulate sulfide levels to correct the elevated bound and acid-labile pools, while maintaining normal levels of free $H_2S$ which is considered vasculo-protective, again, being aware of the multiple sulfide pools. Drugs that redistribute sulfide towards free $H_2S$, and/or decrease total sulfide levels towards normal are optional first steps towards treating the sulfide pathway disturbances involved in ADRD. By understanding the mechanisms of the levels of the various sulfide pools, the inventors can list several alternative or additional mechanistic strategies to alter sulfide levels and treat early pre-symptomatic ADRD (before cognitive symptoms manifest) or symptomatic ADRD.

First, dietary: by decreasing protein, cysteine or homocysteine, sources of $H_2S$ species in the diet, substrate availability for sulfide generation will be lowered, thereby normalizing bound and acid labile sulfide pools. This would preferably include regular plasma sulfide levels monitoring, and adjustment of diets to normalize or rebalance sulfide levels to avoid decreasing sulfide below normal, which would likely be detrimental.

Second Pharmacological: sulfide scavengers such as cyanocobalamin, cobinamide, and SS1-SS30 (as described by Yang C T, et al., Data-Driven Identification of Hydrogen Sulfide Scavengers. Angew Chem Int Ed Engl. 2019 Aug. 5; 58(32):10898-10902. doi: 10.1002/anie.201905580. Epub 2019 Jul. 11. PMID: 31194894; PMCID: PMC6663634, such document incorporated by reference) can be used to reduce $H_2S$ in biological settings. Such sulfide scavengers would be administered at a dose and duration until the level of plasma total sulfide was brought to normal, preferably below 1.70 µM, more preferably below 1.67 µM, most preferably below 1.64 µM.

Third, Downstream targets of sulfide stress can include proteins (persulfidation) and iron clusters. The inventors' previous work has shown that per- and polysulfides can interact with proteins within the vasculature and disrupt solute barrier function, which is an early sign of microvascular disturbance in ADRD. Several possible compartment specific inhibitors of CSE, CBS, MST (enzymes responsible for hydrogen sulfide generation), as well as scavengers of sulfide administered intravenously, intranasally or orally would be therapeutic against ADRD associated sulfide stress while preserving necessary/beneficial effects of sulfides in the cardiovascular system.

Fourth, CSE inhibition. Since the inventors have evidence that plasma sulfide is primarily derived from vascular CSE, blocking vascular CSE represents one therapeutic goal. Several CSE inhibitors could be used in this approach including L-propylarginine (L-PAG, $IC_{50}$=40 uM), L-aminoethoxyvinylglycine (AVG, $IC_{50}$=<1 uM) and β-cyanoalanine (BCA, $IC_{50}$=14 uM). 1157172 (2-[(4-(2,5-dimethoxyanilino)-6-(3-nitroanilino)-1,3,5-triazin-2-yl) sulfanyl]-6-ethoxy-1,3-benzothiazole, $IC_{50}$=30 uM) is both an inhibitor of CSE activity and expression and is an optional therapeutic.

Fifth, CBS inhibition. Because CBS is abundant in the central nervous system and can synergistically produce $H_2S$ from cysteine plus homocysteine, a dietary risk for ADRD, and because B vitamin therapies ($B_6$) can reduce homocysteine burden, CBS inhibitors like hydroxylamine, AOAA, aminooxyacetic acid (AOAA, $IC_{50}$=1 uM) trifluoroalanine and AVG individually and with B vitamins ($B_6$) could represent valuable approaches to reduce pathogenic $H_2S$ species in the setting of ADRD.

Sixth, NO promotor, such as NO generating species/enzymes. Because CSE can be inhibited by NO donors or $NO_2$, nitric oxide pathway species represent additional approaches for inhibiting CSE mediated $H_2S$ release. NO donors like DEA/NO, DETA/NO, Sper/NO used at concentrations up to 50 uM could be used to therapeutically modulate CSE activity in the setting of ADRD. Sodium nitrite therapy (either in its neat or sustained release form) could be used to decrease acid labile, bound sulfane sulfur, and total sulfide levels. Dose ranges for either form of sodium nitrite therapy would be from 165 µg/kg to 1.65 mg/kg.

Pharmaceutical Compositions

The methods described herein can also include the administrations of pharmaceutically acceptable compositions that include the therapeutic, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* $22^{nd}$ Ed., Gennaro, Ed., Lippencott Williams & Wilkins (2012), a well-known reference text in this field, and in the USP/NF (United States Pharmacopeia and the National Formulary), each of which is incorporated by reference. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients,* $8^{th}$ Edition, Sheskey et al., Eds., Pharmaceutical Press (2017), which is incorporated by reference.

The methods described herein can include the administration of a therapeutic, or prodrugs or pharmaceutical compositions thereof, or other therapeutic agents. Exemplary therapeutics include those that reduces plasma total sulfide, and preferably maintains free sulfide at a normal level.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with nontoxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences*, 81(1): 1-10, 1992).

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art (see, e.g., Biesalski, U.S. Pat. No. 5,112,598, and Biesalski, U.S. Pat. No. 5,556,611).

Formulations for sublingual administration can also be used, including powders and aerosol formulations. Exemplary formulations include rapidly disintegrating tablets and liquid-filled soft gelatin capsules.

Dosing Regimes

The present methods for treating ADRD are carried out by administering a therapeutic for a time and in an amount sufficient to result in decreased plasma total sulfide level, acid-labile sulfide level, and/or bound sulfide level.

The amount and frequency of administration of the compositions can vary depending on, for example, what is being administered, the state of the patient, and the manner of administration. In therapeutic applications, compositions can be administered to a patient suffering from ADRD in an amount sufficient to relieve or least partially relieve the symptoms of the ADRD and its complications. The dosage is likely to depend on such variables as the type and extent of progression of the ADRD, the severity of the ADRD, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the ADRD or slowing its progression.

The amount of therapeutic per dose can vary. For example, a subject can receive from about 0.1 µg/kg to about 10,000 µg/kg. Generally, the therapeutic is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 µmol of therapeutic (e.g., 0.1-25 µmol or 0.4-20 µmol).

The plasma concentration of therapeutic can also be measured according to methods known in the art. Exemplary peak plasma concentrations of therapeutic can range from 0.05-10 µM, 0.1-10 µM, 0.1-5.0 µM, or 0.1-1 µM. Alternatively, the average plasma levels of therapeutic can range from 400-1200 µM (e.g., between 500-1000 µM) or between 50-250 µM (e.g., between 40-200 µM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the tests and pharmaceutical compositions of the invention described herein can be used together with a set of instructions, i.e., to form a kit. The kit may include instructions for use of a test for biochemical sulfide level, and pharmaceutical compositions as a therapy as described herein. For example, the instructions may provide dosing and therapeutic regimes for use of the compounds of the invention to reduce symptoms and/or underlying cause of the ADRD.

ABBREVIATIONS

AA African America
AD Alzheimer's disease
ADAS-cog Alzheimer's disease Assessment Scale
ADRD Alzheimer's disease and related dementias
AT(N) amyloid, p-Tau and neurodegeneration
AUC Area under the curve
BBB Blood brain barrier
CBS Cystathionine β-synthase
CSE Cystathionine γ-lyase
CSEKO Cystathionine γ-lyase-deficient mice
FLAIR 3D fluid-attenuated inversion recovery
HPLC High pressure liquid chromatograph
H2S Hydrogen Sulfide
MANOVA Multivariate analysis of variance
MBB Monobromobiamine
Na—F Sodium Fluorescein
NO Nitric oxide
p-Tau Phosphorylated-Tau
ROC Receiver-operating characteristic
TCA Trichloroacetic acid
WT Wildtype The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method of diagnosing and treating Alzheimer's disease and related dementias (ADRD) comprising:
    obtaining a plasma sample from the patient;
    determining a level of a biochemical sulfide in the plasma sample from the patient, the biochemical sulfide being one of acid-labile sulfide, bound sulfide, and total sulfide;
    diagnosing the patient with ADRD when biochemical sulfide is above a cutoff; and administering an effective amount of a sulfide reducer to the diagnosed patient, wherein:
    the sulfide reducer is a CSE inhibitor and includes one of L-propylarginine, L-aminoethoxyvinylglycine, I157172 (2-[(4-(2,5-dimethoxyanilino)-6-(3-nitroanilino)-1,3,5-triazin-2-yl) sulfanyl]-6-ethoxy-1,3-benzothiazole); or
    the sulfide reducer is a CBS inhibitor and includes one of hydroxylamine, aminooxyacetic acid, trifluoroalanine, L-aminoethoxyvinylglycine, and both L-aminoethoxyvinylglycine and pyridoxamine; or
    the sulfide reducer is an MST inhibitor and includes XMU-MP-1 (4-((5,10-dimethyl-6-oxo-6,10-dihydro-5H-pyrimido[5,4-b]thieno[3,2-e][1,4]diazepin-2-yl) amino)benzenesulfonamide).

2. The method of claim 1, wherein the sulfide reducer is administered at a dose and a duration until the level of biochemical sulfide was brought to below 1.70 µM.

3. The method of claim 2, wherein the effective amount of sulfide reducer is a dose such that when administered the patient plasma reaches an $IC_{50}$ for the sulfide reducer.

* * * * *